(12) United States Patent
Oguni (10) Patent No.: US 7,488,574 B2
(45) Date of Patent: Feb. 10, 2009

(54) APPARATUS AND METHOD FOR CELL ANALYSIS

(75) Inventor: Shinichiro Oguni, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 11/083,281

(22) Filed: Mar. 17, 2005

(65) Prior Publication Data

US 2005/0272026 A1     Dec. 8, 2005

(30) Foreign Application Priority Data

Mar. 17, 2004   (JP) .............................. 2004-075567

(51) Int. Cl.
*C12Q 1/00*   (2006.01)
(52) U.S. Cl. .......................................................... 435/4
(58) Field of Classification Search ...................... 435/4
See application file for complete search history.

(56) References Cited

U.S. PATENT DOCUMENTS 5,434,081 A    7/1995   Maekawa 5,656,499 A  *  8/1997   Chupp et al. ................... 436/43

FOREIGN PATENT DOCUMENTS

JP        2002-148261 A       5/2002

OTHER PUBLICATIONS

Bochner BS et al (1997) Studies of cell adhesion and flow cytometric analyses of degranulation, surface phenotype, and viability using human eosinophils, basophils, and mast cells. Methods, vol. 13, pp. 61-68.*
Keeney, M. et al., "Single Platform Flow Cytometric Absolute CD34 + Cell Counts Based on the ISHAGE Guidelines", *Cytometry (Communications in Clinical Cytometry)*, vol. 34, issue 2, 1998, pp. 61-70.

* cited by examiner

*Primary Examiner*—Maryam Monshipouri
(74) *Attorney, Agent, or Firm*—Brinks Hofer Gilson & Lione (57) ABSTRACT

A cell analysis apparatus includes a test sample preparation part for preparing a test sample by treating an analyte with a dye for staining an intracellular substance of cells in the analyte, a detector for detecting scattered light and fluorescence from each cell in the test sample, and a controller for identifying living mononuclear cells based on the scattered light and the fluorescence detected by the detector. A cell analysis method includes preparing a test sample by treating the analyte with a dye for staining an intracellular substance of cells in the analyte; detecting scattered light and fluorescence from each cell in the test sample; and identifying living mononuclear cells based on the scattered light and the fluorescence detected.

11 Claims, 9 Drawing Sheets

APPARATUS AND METHOD FOR CELL ANALYSIS

This application claims priority under 35 U.S.C. § 119 to Japanese Patent Application No. 2004-075567 filed Mar. 17, 2004, the entire content of which is hereby incorporated by reference.

BACKGROUND OF THE INVENTION

1. Field of the Invention

The invention relates to an apparatus and method for measurement of mononuclear cells contained in analytes.

2. Description of the Related Art

Cell therapy such as stem cell transplantation and donor lymphocyte infusion uses stem cells, lymphocytes or the like for cell transplantation into patients. Stem cells and lymphocytes (hereinafter generically referred to as "mononuclear cells") for use in cell therapy are mainly contained in blood (e.g. peripheral blood and cord blood) and bone marrow. Hereinafter, mononuclear cell-containing fluid for use in cell therapy, such as blood and bone marrow, is referred to as "cell material."

Collected cell materials undergo many processes (e.g. removal of cells unnecessary for therapy from the cell materials, freezing and thawing of the cell materials, and the like) before they are transplanted into patients. In such cell materials, therefore, cells necessary for therapy can be damaged. As used herein, the term "damaged cells" refers to dead cells that have their cell membrane damaged and are made nonviable by an influence such as "changes over time after the collection," "poor storage conditions," "the process of removing unnecessary cells" and " the process of freezing and thawing the cell material." Such dead cells of mononuclear cells (hereinafter referred to as dead mononuclear cells) cannot contribute to engraftment success after transplantation, and thus cell materials rich in dead mononuclear cells are improper to cell therapy.

Therefore, a condition that cell materials should satisfy for effective cell therapy is to contain plenty of living cells of mononuclear cells (hereinafter referred to as living mononuclear cells). Thus, it is important to check the viability of mononuclear cells in cell materials before they are used in cell therapy, and therefore, there is a need to identify living mononuclear cells in cell materials.

Japanese Patent Application Laid-Open (JP-A) No. 2002-148261 discloses a method of classifying and counting abnormal cells, in which abnormal cells such as damaged leukocytes with their cell membrane damaged are classified and counted while leukocytes are measured. In this method, a flow cytometer is used to determine the intensities of fluorescence and scattered light with respect to each cell in blood treated with a fluorescent dye so that leukocytes and damaged leukocytes can be identified based on the intensities of the fluorescence and the scattered light. In the specification of the publication, the term "damaged leukocytes" refers to leukocytes whose cell membrane is damaged by an influence such as changes over time after collection and poor storage conditions.

However, the specification of the publication doesn't disclose the identification of living mononuclear cells including stem cells.

A known method of identifying living mononuclear cells uses 7-aminoactinomycin D (7-AAD), fluorescence-labeled CD34 and fluorescence-labeled CD45 (Michael Keeney, Ian Chin-Yee, Karin Weir, Jan Popma, Rakash Nayar, D. Robert Sutherland, "Single platform flow cytometric absolute CD34+cell counts based on the ISHAGE guidelines," Cytometry Wiley-Liss, Inc., 1998, Volume 34, Issue 2, P. 61-70). The 7-AAD is a fluorescent dye for staining of nucleic acid. With this dye, dead cells are more stained than living cells, so that the living cells can be identified separately from the dead cells based on the difference in the degree of 7-AAD staining. CD34 is an antibody to a stem cell surface antigen, and CD45 is an antibody to a leukocyte cell surface antigen. Thus, living mononuclear cells can be identified using 7-aminoactinomycin D (7-AAD) and CD34 or CD45 at the same time.

However, the above method involves a complicated process including the modification of the stem or leukocyte cell surface antigen through antigen-antibody reaction at the time of preparing test samples, and it takes much time.

SUMMARY OF THE INVENTION

The present invention provides a cell analysis apparatus and method for identifying living mononuclear cells in analytes more easily and rapidly than the conventional techniques.

A first aspect of the present invention relates to a cell analysis apparatus comprising: a test sample preparation part for preparing a test sample by treating an analyte with a dye for staining an intracellular substance of the cells in the analyte; a detector for detecting scattered light and fluorescence from each cell in the test sample; and a controller for identifying living mononuclear cells based on the scattered light and the fluorescence detected by the detector.

A second aspect of the present invention relates to a cell analysis method comprising: (a) preparing a test sample by treating an analyte with a dye for staining an intracellular substance of the cells in the analyte; (b) detecting scattered light and fluorescence from each cell in the test sample; and (c) identifying living mononuclear cells based on the scattered light and the fluorescence detected in the step(b).

DESCRIPTION OF PREFERRED EMBODIMENTS

A description is provided below of a cell analysis apparatus according to an embodiment of the invention. In the cell analysis apparatus, first, an analyte is subjected to a fluorescent staining process in which a diluent and a dyeing solution are added to the analyte to prepare a test sample. The prepared test sample is then irradiated with a laser beam, and scattered light and fluorescence emitted from the test sample are detected. Cells contained in the analyte are identified based on the detected scattered light and fluorescence. In the cell analysis apparatus, blood is used as an analyte.

Figure 1:
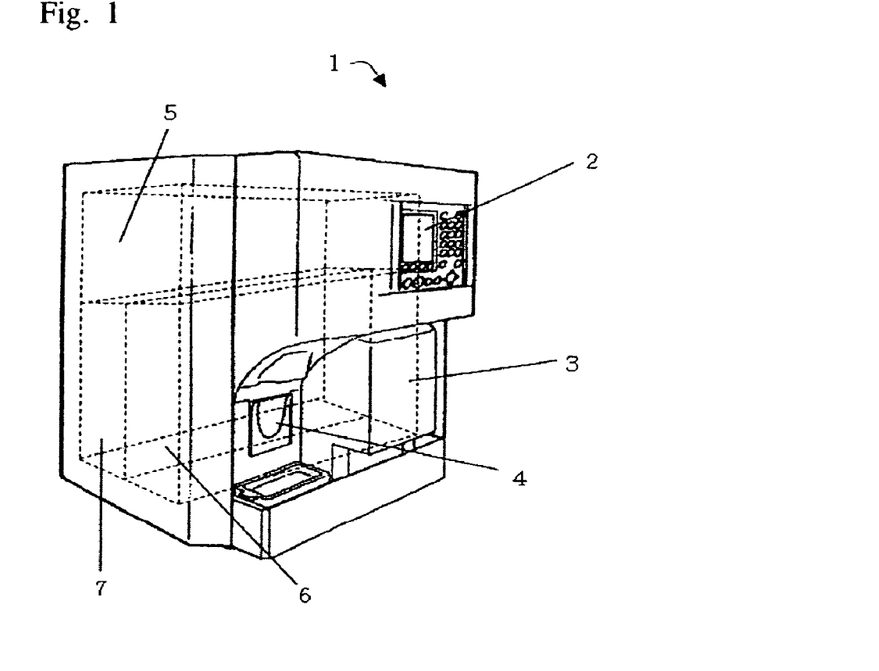
FIG. 1 is a diagram illustrating the configuration of a cell analysis apparatus according to an embodiment of the invention.

In FIG. 1, a solid line is used to show the appearance of a cell analysis apparatus 1, and a broken line is used to schematically show the configuration of the interior of the apparatus. As shown by the solid line, a liquid-crystal touch panel 2 for setting various inputs and outputting measurement results, a test sample preparation part cover 3, and a start switch 4 are disposed on the front of the apparatus 1. As shown by the broken line, a control unit 5 for controlling the operating status of the apparatus and the analysis process is disposed at an upper portion of the interior of the apparatus 1. A test sample preparation part 6 for preparing test samples is disposed on the front side of the lower portion. A measurement part 7 for detecting signals from the test sample is disposed on the back side of the lower portion.

Figure 2:
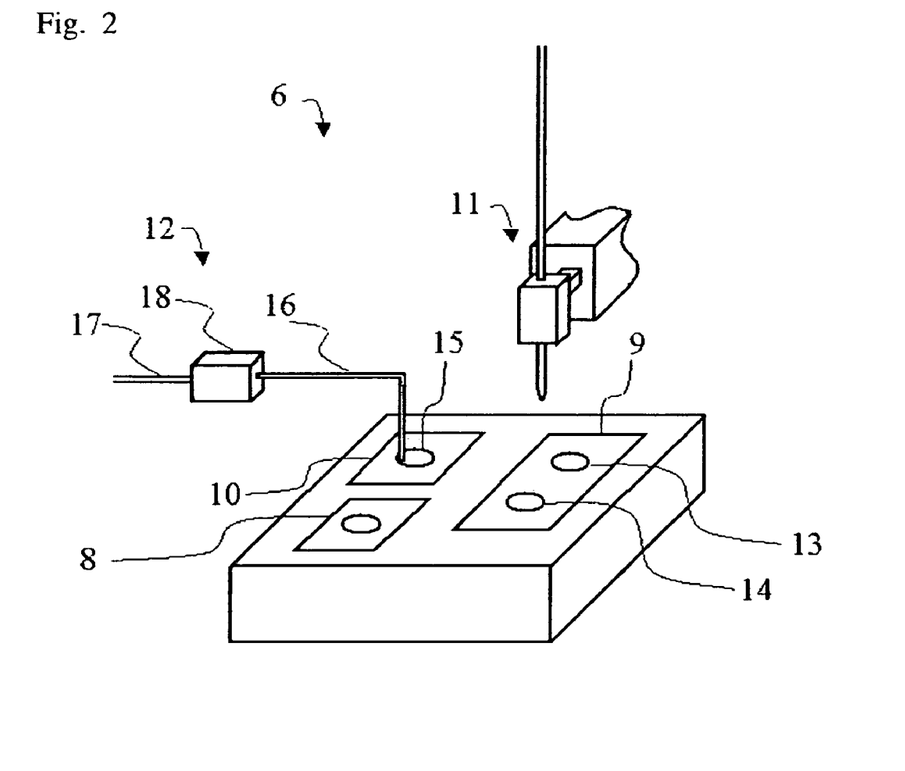
FIG. 2 is a diagram illustrating a test sample preparation part of a cell analysis apparatus according to an embodiment of the invention.
Figure 3:
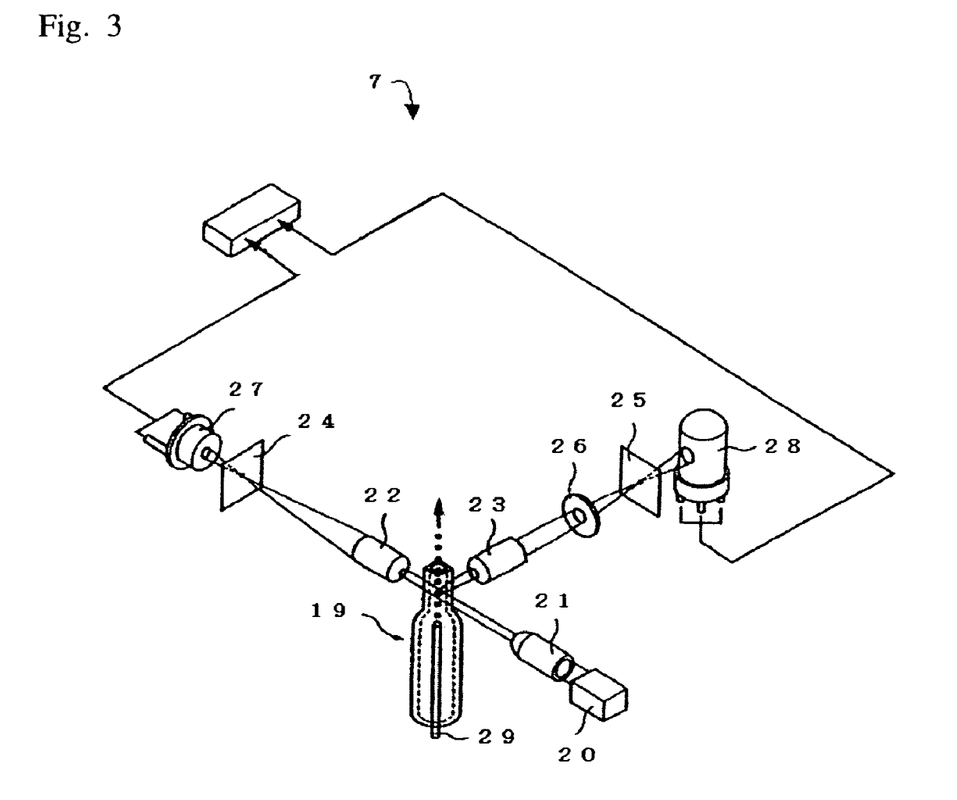
FIG. 3 is a diagram illustrating a measurement part of a cell analysis apparatus according to an embodiment of the invention.

FIG. 2 is a schematic diagram showing the test sample preparation part 6. The test sample preparation part 6 is comprised of an analyte setting part 8, a reagent setting part 9, a staining part 10, a dispensing device 11, and a liquid transporting device 12. When the test sample preparation part cover 3 shown in FIG. 1 is opened, an analyte container containing an analyte can be set in the analyte setting part 8, and a container 13 containing a dyeing solution and a container 14 containing a diluent can also be set in the reagent setting part 9, respectively. A container 15 is set in the staining part 10, where the analyte is mixed with the dyeing solution and the diluent to prepare a test sample. The staining part 10 also includes a temperature control system for keeping the solution in the container 15 at a constant temperature and a stirring mechanism for stirring the solution in the container 15, though they are not shown in the drawings. The dispensing device 11 is adapted to suck and eject a predetermined amount of liquid through its tip, and also dispensing device 11 is vertically and horizontally movable by a driving device (not shown). The liquid transporting device 12 is comprised of a suction tube 16 for sucking the test sample, a liquid transporting pipe 17 for transporting the test sample sucked from the suction tube 16 to the measurement part 7 as shown in FIG. 3, and a pump 18 for sucking the test sample and transporting the test sample to the measurement part 7. The suction tube 16 is inserted into the container 15 set in the staining part 10 so as to suck a predetermined amount of the test sample. The sucked test sample is transported to the measurement part 7 through the transporting pipe 17.

Figure 4:
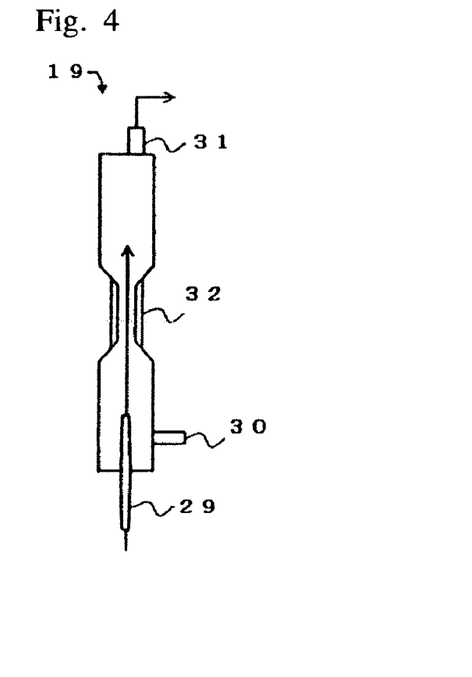
FIG. 4 is a diagram illustrating a sheath flow cell part of a cell analysis apparatus according to an embodiment of the invention.

FIG. 3 is a schematic diagram showing the measurement part 7. The measurement part 7 is comprised of a sheath flow cell 19, a laser beam source 20, a condenser lens 21, converging lenses 22 and 23, pinholes 24 and 25, a filter 26, a photodiode 27, and a photomultiplier tube 28. The sheath flow cell 19 is provided to feed the test sample, which has been prepared in the test sample preparation part 6 as shown in FIG. 2. Referring to FIG. 4, the sheath flow cell 19 also is comprised of a sample nozzle 29 for jetting the test sample upward to a capillary part 32, a sheath liquid inlet 30 and a liquid outlet 31. The laser beam source 20 emits a red laser beam with a wavelength of 633 nm. The converging lenses 22 and 23 collects optical information such as forward scattered light and side fluorescence, which are obtained from each and every cell in the test sample receiving the laser beam. The photodiode 27 receives the forward scattered light, photoelectrically converts it, and outputs electric signals from it. The photomultiplier tube 28 receives the side fluorescence, photoelectrically converts it, and outputs electric signals from it. Each output signal is transmitted to the control unit 5.

Figure 5:
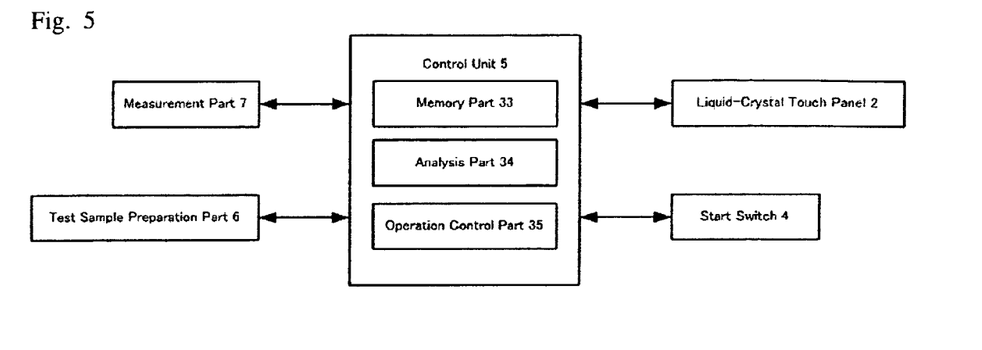
FIG. 5 is a diagram illustrating the relationship between a control unit and any other part of a cell analysis apparatus according to an embodiment of the invention.

FIG. 5 is a block diagram showing the configuration of the control unit 5 and the relationship between the control unit 5 and each of other parts of the apparatus. The control unit 5 includes a microcomputer having a central processing unit (CPU) and storage devices such as ROM and RAM, a circuit for processing the signals transmitted from the measurement part 7, and so on. The control unit 5 serves the functions: a memory part 33, an analysis part 34 and an operation control part 35. The memory part 33 stores analysis programs for performing analysis of the signals derived from the cells in the test sample and control programs for controlling the operation of each part of the apparatus. The memory part 33 also stores the signal data detected by the measurement part 7 and the result of processing by the analysis programs. Based on the analysis programs, the analysis part 34 analyzes the signals detected by the measurement part 7 to produce data concerning each cell contained in the test sample. The data produced by the analysis part 34 is output to the liquid-crystal touch panel 2. The operation control part 35 controls the operation of each part of the apparatus based on the control programs stored in the memory part 33.

The operation of the apparatus is described in detail below. First, the operator sets an analyte and reagents in the predetermined positions of the test sample preparation part 6. The analyte can be set in the analyte setting part 8 of the test sample preparation part 6 as shown in FIG. 2, when the test sample preparation part cover 3 shown in FIG. 1 is opened. The reagents such as a dyeing solution and a diluent can be set in the container 13 and the container 14, respectively, in the reagent setting part 9 of the test sample preparation part 6, when the test sample preparation part cover 3 is opened.

Figure 6:
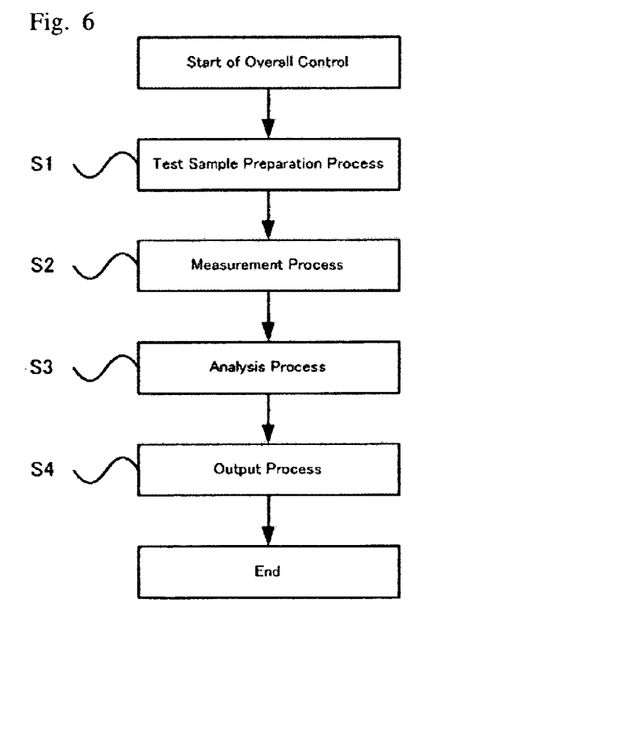
FIG. 6 is a diagram illustrating a flow of overall control in a cell analysis apparatus according to an embodiment of the invention.

When the analyte and the reagents are set, and the start switch 4 is turned on, the overall control is started. FIG. 6 is a flow chart showing the overall control by the control programs. When the start switch is turned on, S1 (test sample preparation process), S2 (measurement process), S3 (analysis process), and S4 (output process) are sequentially performed. The test sample preparation part 6, the measurement part 7 and the analysis part 34 are controlled based on the control programs, and a series of operation is automatically performed. The processes S1, S2, S3, and S4 are described below.

S1 (Test Sample Preparation Process)

The operation of the test sample preparation part 6 in the test sample preparation process is described referring to FIG. 2. First, the dispensing device 11 sucks the analyte from the analyte container set in the analyte setting part 8 and dispenses 4.5 μL of the analyte to the container 15 set in the staining part 10. The dispensing device 11 then sucks the diluent from the container 14 set in the reagent setting part 9 and dispenses 0.8955 mL of the diluent to the container 15 set in the staining part 10. The dispensing device 11 also sucks the dyeing solution from the container 13 set in the reagent setting part 9 and dispenses 18 μL of the dyeing solution to the container 15 set in the staining part 10. Thereafter, the staining part 10 keeps the temperature of the container 15 at 37 C. while stirring is performed for 31 seconds, so that a test sample is prepared in the container 15. In the preparation of the test sample, RET-SEARCH(II)DYE and RET-SEARCH (II)DILUENT both manufactured by Sysmex Corporation are used as the dyeing solution and the diluent, respectively. RET-SEARCH(II)DYE contains a fluorescent dye capable of specifically staining nucleic acids in cells, which has the property wherein fluorescence is excited by the application of a laser beam with a wavelength of around 630 nm.

Upon preparation of the test sample, 2.8 μL of the test sample is sucked from the container 15 in the staining part 10 by the liquid transporting device 12 and sent tot the sheath flow cell 19 in the measurement part 7.

S2 (Measurement Process)

The operation of the measurement part 7 in the measurement process is described referring to FIGS. 3 and 4. The test sample as prepared in the test sample preparation part 6 is introduced into the sheath flow cell 19, and the test sample is ejected into the sheath flow cell 19 through the sample nozzle 29. At the same time, a sheath liquid is ejected into the sheath flow cell 19 through the sheath liquid inlet 30. Thus, the test sample is surrounded by the sheath liquid in the sheath flow cell and is allowed to narrow and flow in the capillary part 32.

The laser beam emitted from the laser beam source 20 is concentrated by the condenser lens 21 and then applied to the sample flow in the capillary part 32. The forward scattered light emitted from each and every cell in the test sample receiving the laser beam is converged by the converging lens 22 and passes through the pinhole 24. The side fluorescence is converged by the converging lens 23 and passes through the filter 26 and the pinhole 25. The photodiode 27 receives the forward scattered light, photoelectrically converts it, and outputs it as a forward scattered light signal. The photomultiplier tube 28 receives the side fluorescence, photoelectrically converts it, and outputs it as a side fluorescence signal. Each signal is transmitted to the control unit 5 and stored as data per cell in the memory part 33.

S3 (Analysis Process)

Figure 7:
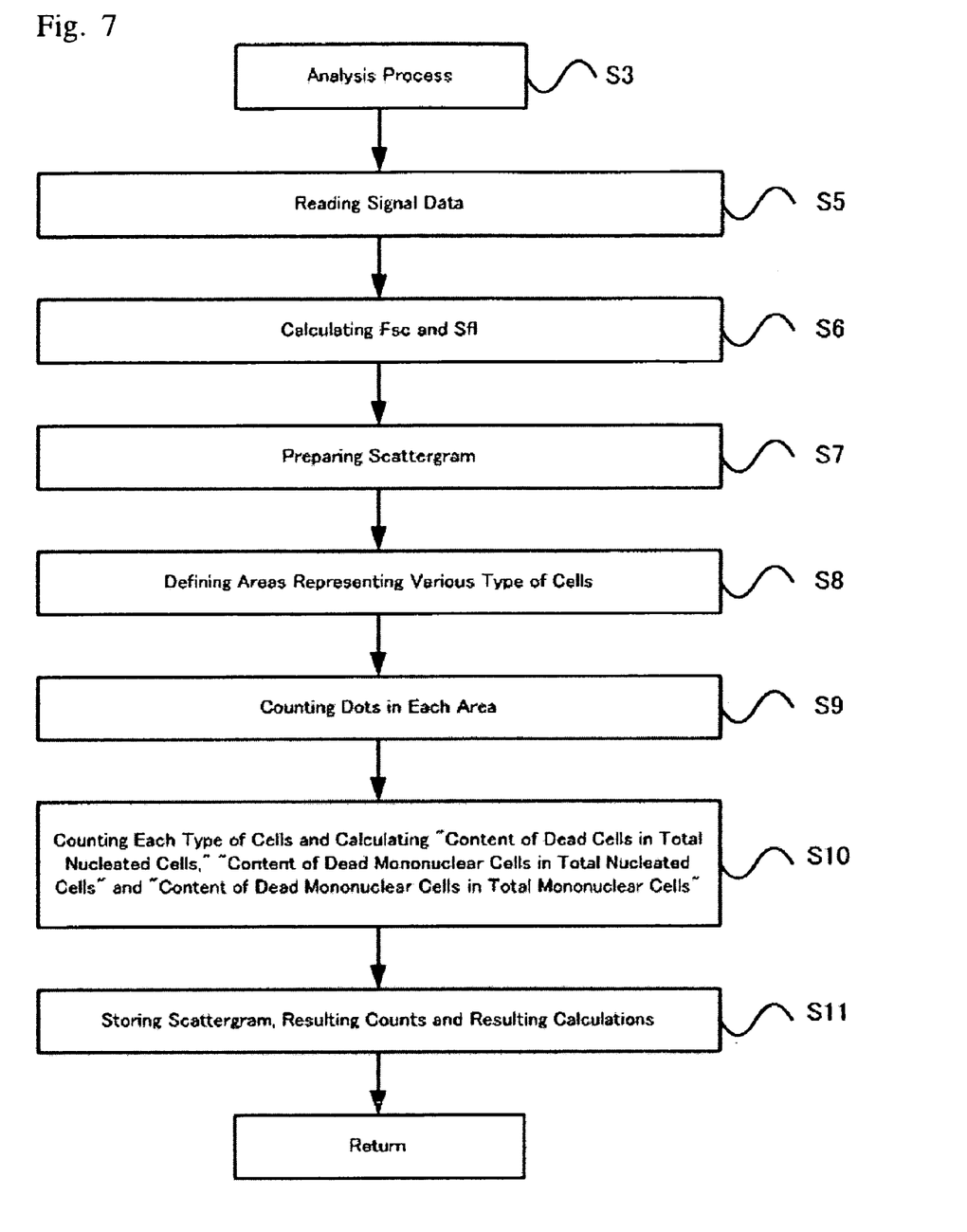
FIG. 7 is a diagram illustrating a flow of an analysis process in a cell analysis apparatus according to an embodiment of the invention.

When the forward scattered light signal and the side fluorescence signal are detected by the measurement process S2, each signal is subsequently analyzed by the analysis part 34 based on the analysis programs. The operation according to the analysis programs in S3 is described referring to the flow chart as shown in FIG. 7, which includes each of the following steps:

S5: The data of the forward scattered light signals and the side fluorescence signals, which are detected from each cell in the test sample, are read from the memory part 33. The process then proceeds to S6.

S6: The intensity of the forward scattered light (Fsc) and the intensity of the side fluorescence (Sfl) are calculated based on the forward scattered light signals and the side fluorescence signals derived from each cell in the test sample. The process then proceeds to S7.

S7: A scattergram is prepared using, as parameters, Fsc and Sfl per cell calculated in S6. In the preparation, a two-dimensional coordinate with Fsc and Sfl axes is first developed. The coordinate position of each cell in the test sample is then determined based on Fsc and Sfl calculated in S6, so that a scattergram is prepared using Fsc and Sfl as parameters. The process then proceeds to S8.

Figure 8:
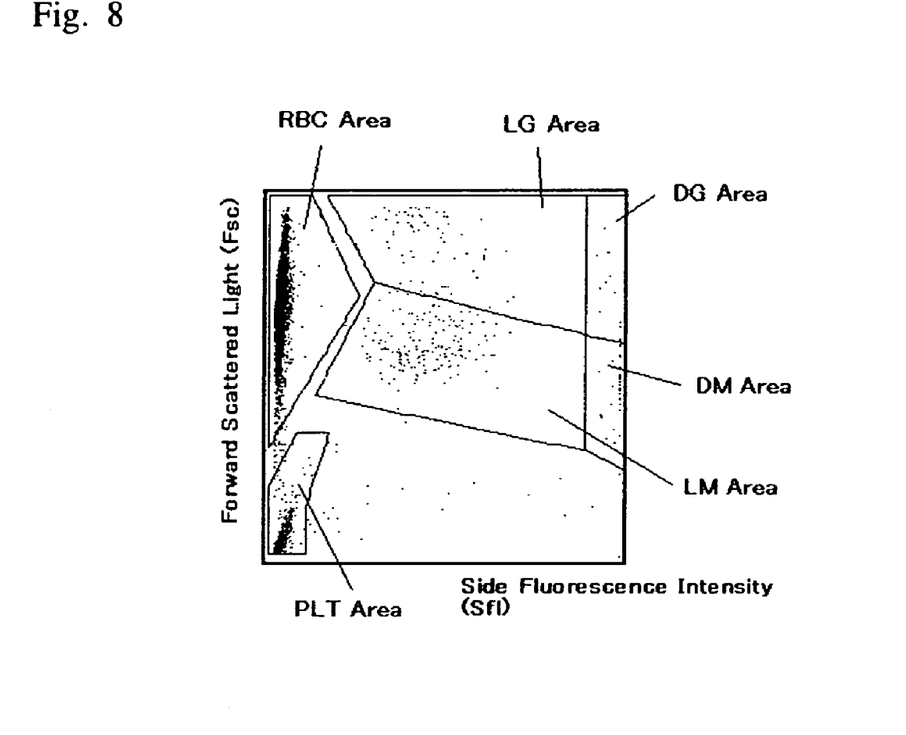
FIGS. 8, 9A, 9B, 10A, 10B, 11A, 11B, and 12 are diagrams each showing a two-dimensional scattergram prepared by a cell analysis apparatus according to an embodiment of the invention.

S8: An area that represents living mononuclear cells (referred to as LM area), an area that represents dead mononuclear cells (referred to as DM area), an area that represents living cells of granulocytes (hereinafter referred to as living granulocytes) (referred to as LG area), an area that represents dead cells of granulocytes (hereinafter referred to as dead granulocytes) (referred to as DG area), an area that represents red blood cells (referred to as RBC area), and an area that represents blood platelets (referred to as PLT area) are each defined in the prepared scattergram. FIG. 8 shows these areas defined in the scattergram. The definition of LM, DM, LG, DG, RBC, and PLT areas is experimentally made by measurement of test samples previously confirmed as containing living mononuclear cells, dead mononuclear cells, living granulocytes, dead granulocytes, red blood cells, and blood platelets, respectively. Among the cells contained in the sample, therefore, living mononuclear cells are found in LM area, dead mononuclear cells in DM area, living granulocytes in LG area, dead granulocytes in DG area, red blood cells in RBC area, and blood platelets in PLT area. The data of each area are stored in the memory part 33 and read according to the analysis programs in S8 to be applied to the scattergram. The process then proceeds to S9.

S9: Dots in each area are counted. The process then proceeds to S10.

S10: The number of the dots counted in each area in S9 corresponds to the number of each type of cells contained in analytes. Based on the number of the dots counted in each area in S9, therefore, the number of each type of cells is determined. Based on the counts of the cells, "the content of dead cells in the total nucleated cells," "the content of dead mononuclear cells in the total nucleated cells"and " the content of dead mononuclear cells in the total mononuclear cells" are also calculated. The process then proceeds to S11. As used herein, the term "the total nucleated cells" refers to all the cells found in the nucleated cell-representing areas (LM, DM, LG, and DG areas). As used herein, the term "dead cells" refers to all the cells found in the dead cell-representing areas (DM and DG areas). As used herein, the term "the total mononuclear cells" refers to all the cells found in the mononuclear cell-representing areas (LM and DM areas).

S11: The data are stored which include the data of the scattergram prepared in S7 and S8, and the resulting count data and calculation data obtained in S10.

As mentioned above, FIG. 8 is a diagram for illustrating the scattergram prepared in S7 and S8. The horizontal axis of the scattergram represents Sfl, and the vertical axis Fsc. On the horizontal axis, the Sfl value increases, as it goes to the right. On the vertical axis, the Fsc value increases, as it goes upward. Living mononuclear cells are found in LM area, dead mononuclear cells in DM area, living granulocytes in LG area, dead granulocytes in DG area, red blood cells in RBC area, and blood platelets in PLT area. Dead cells have their cell membrane damaged, and therefore, when stained with a nucleic acid-staining dye, dead cells are more stained with the fluorescent dye than living cells. Thus, the intensity of the fluorescence detected from dead cells is higher than that detected from living cells. Therefore, the dead cell-representing areas (DM and DG areas) are positioned to have higher fluorescence intensities than those of the living cell-representing areas (LM, LG, RBC, and PLT areas). Red blood cells and blood platelets have no nucleus (a nucleate cells) and thus are less stained with a nucleic acid-staining dye. Therefore, the a nucleate cell-representing areas (RBC and PLT areas) are positioned to have lower fluorescence intensities than those of the nucleus-containing cell (nucleated cell)-representing areas (LM, DM, LG, and DG areas). Since read blood cells are larger than blood platelets, the read blood cell-representing area (RBC area) is positioned to have higher forward scattered light intensities than those of the blood platelet-representing area (PLT area). Among leukocytes, granulocytes are larger than mononuclear cells. Thus, the granulocyte-representing areas (LG and DG area) are generally positioned to have higher forward scattered light intensities than those of the mononuclear cell-representing areas (LM and DM areas).

S4 (Output Process)

The scattergram obtained in S3, the result of counting each type of cells, and the results of calculating "the content of dead cells in the total nucleated cells," "the content of dead mononuclear cells in the total nucleated cells," and "the content of dead mononuclear cells in the total mononuclear cells" are output and displayed on the liquid-crystal touch panel 2. The "content of dead mononuclear cells in the total mononuclear cells" represents the ratio of the dead mononuclear cells in the total mononuclear cells, and thus this value can be used as the viability of mononuclear cells in evaluation. It can be determined that the lower the value, the higher the viability of the mononuclear cells in the analyte.

In the cell analysis apparatus 1, the forward scattered light and the fluorescence are detected from the cells in the test sample which is subjected to the fluorescent staining treatment substantially using a single type of fluorescent dye, and based on them, living mononuclear cells, dead mononuclear cells, living granulocytes, dead granulocytes, red blood cells, and blood platelets are identified respectively. In other words, the cell analysis apparatus 1 does not use different fluorescent dyes in order to classify the cells and to determine whether the cells are alive or dead, and it allows a distinction between different types of cells or between living and death of cells by detecting a single type of fluorescence. Therefore, as compared with other apparatuses involving detection of different types of fluorescence, the present apparatus can work with a reduced number of reagent types and with a simplified mechanism or configuration.

Some analytes were subjected to the analysis using the cell analysis apparatus 1 as described above. The results of the analysis are shown below as examples.

MEASUREMENT EXAMPLE 1

Two types of human peripheral blood ((I) and (II)) were used as analytes in this measurement example. The different types of peripheral blood were collected from patients with different diseases. The leukocytes of peripheral blood (I) had a very high content of lymphocytes. The leukocytes of peripheral blood (II) had a very high content of granulocytes.

While collected peripheral blood is allowed to stand at room temperature, the content of dead cells in the peripheral blood generally increases with time. In this measurement example, peripheral bloods (I) and (II) were each collected and allowed to stand at room temperature for 2 or 24 hours before used as analytes.

Figure 9:
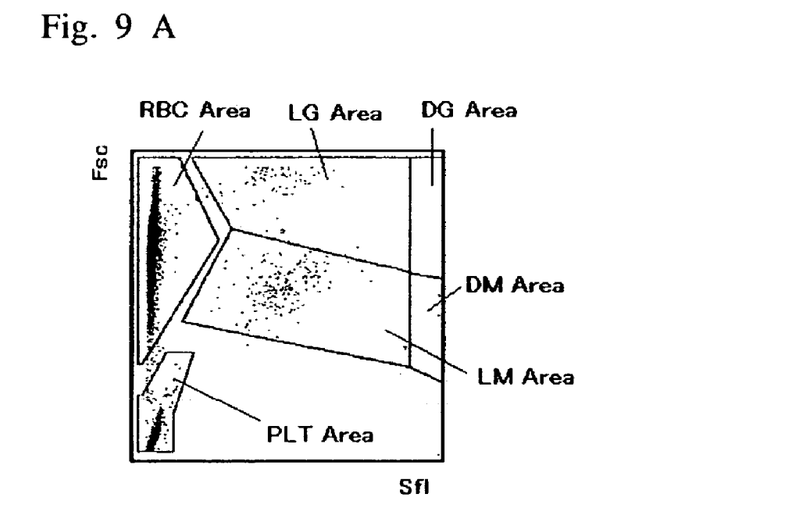
Figure 10:
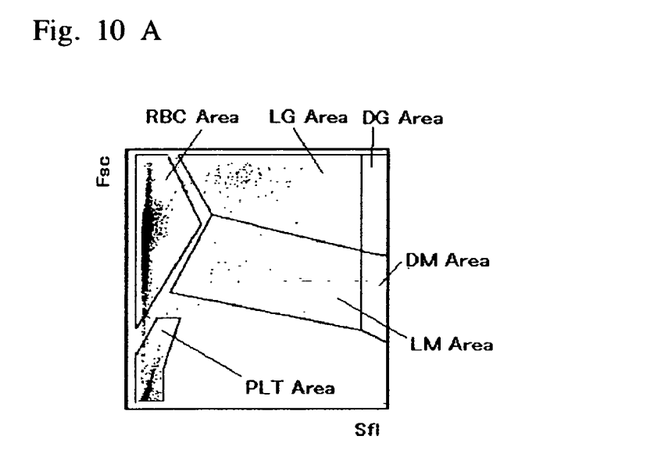

The scattergrams as shown in FIGS. 9A, 9B, 10A, and 10B were obtained using the cell analysis apparatus 1 as described above. FIGS. 9A and 9B show the results of the measurement using peripheral blood (I) as an analyte, wherein FIG. 9A shows the result of the measurement in which the peripheral blood was allowed to stand at room temperature for 2 hours after the collection, and FIG. 9B shows the result of the measurement in which the peripheral blood was allowed to stand at room temperature for 24 hours after the collection. FIGS. 10A and 10B show the results of the measurement using peripheral blood (II) as an analyte, wherein FIG. 10A shows the result of the measurement in which the peripheral blood was allowed to stand at room temperature for 2 hours after the collection, and FIG. 10B shows the result of the measurement in which the peripheral blood was allowed to stand at room temperature for 24 hours after the collection. As mentioned above, the horizontal axis of each scattergram represents Sfl, and the vertical axis Fsc. On the horizontal axis, the Sfl value increases, as it goes to the right. On the vertical axis, the Fsc value increases, as it goes upward.

Table 1 shows the count values obtained in step S10 of the analysis process using the cell analysis apparatus 1 as described above, which include "the number of living mononuclear cells," "the number of dead mononuclear cells," "the number of living granulocytes," and "the number of dead granulocytes." Each value with respect to each item in Table 1 is based on the count of dots found in LM, DM, LG, or DG area on each of the scattergrams of FIGS. 9A, 9B, 10A, and 10B. In Table 1, "the number of living mononuclear cells" is represented by LM, "the number of dead mononuclear cells" by DM, "the number of living granulocytes" by LG, and "the number of dead granulocytes" by DG.

In Table 1, column (I) shows the case of peripheral blood (I) used as an analyte in the measurement, and column (II) shows the case of peripheral blood (II) used as an analyte in the measurement. In Table 1, column A shows the results of measurement of the peripheral blood that was allowed to stand at room temperature for 2 hours after the collection, and column B shows the results of measurement of the peripheral blood that was allowed to stand at room temperature for 24 hours after the collection.

TABLE 1

| | Number of Cells Contained Per 1 μL of Analyte | | | |
| --- | --- | --- | --- | --- |
| | (I) | | (II) | |
| | A | B | A | B |
| LM | 14552 | 13640 | 970 | 905 |
| DM | 172 | 1084 | 0 | 65 |
| LG | 5336 | 4907 | 5019 | 3675 |
| DG | 0 | 429 | 0 | 1344 |

Referring to FIGS. 9A, 9B, 10A, and 10B, and Table 1, a comparison between columns A and B indicates that the number of dead cells (dead mononuclear cells and dead granulocytes) is greater in column B than in column A in both cases. FIG. 9B and column B of (I) in Table 1 indicate that the number of dead mononuclear cells predominantly increases, while FIG. 10B and-column B of (II) in Table 1 indicate that the number of dead granulocytes predominantly increases.

Table 2 shows the values calculated in step S10 of the analysis process using the cell analysis apparatus 1 as described above, which include "the content of dead cells in the total nucleated cells," "the content of dead mononuclear cells in the total nucleated cells" and "the content of dead mononuclear cells in the total mononuclear cells." Each value with respect to each item in Table 2 is calculated according to the formulae as shown below from "the number of living mononuclear cells," "the number of dead mononuclear cells," "the number of living granulocytes," and "the number of dead granulocytes" in Table 1. Formula 1 is for the calculation of "the content of dead cells in the total nucleated cells." Formula 2 is for the calculation of "the content of dead mononuclear cells in the total nucleated cells." Formula 3 is for the calculation of "the content of dead mononuclear cells in the total mononuclear cells." The "content of dead mononuclear cells in the total mononuclear cells" represents the ratio of the dead mononuclear cells in the total mononuclear cells. Thus, it can be determined that the smaller the value, the higher the viability of the mononuclear cells in the analyte. In the formulae, "the number of living mononuclear cells" is represented by LM, "the number of dead mononuclear cells" by DM, "the number of living granulocytes" by LG, and "the number of dead granulocytes" by DG.

(DM+DG)/(LM+LG+DM+DG)×100(%)   Formula 1:

DM/(LM+LG+DM+DG)×100(%)   Formula 2:

DM/(LM+DM)×100(%)   Formula 3:

In Table 2, column (I) shows the case of peripheral blood (I) used as an analyte in the measurement, and column (II) shows the case of peripheral blood (II) used as an analyte in the measurement. In Table 2, column A shows the results of measurement of the peripheral blood that was allowed to stand at room temperature for 2 hours after the collection, and column B shows the results of measurement of the peripheral blood that was allowed to stand at room temperature for 24 hours after the collection.

TABLE 2

|  | (I) | | (II) | |
| --- | --- | --- | --- | --- |
|  | A | B | A | B |
| Content of Dead Cells in Total Nucleated Cells (%) | 0.8 | 7.5 | 0.0 | 23.5 |
| Content of Dead Mononuclear Cells in Total Nucleated Cells (%) | 0.8 | 5.4 | 0.0 | 1.1 |
| Content of Dead Mononuclear Cells in Total Mononuclear Cells (%) | 1.2 | 7.4 | 0.0 | 6.7 |

In both columns (I) and (II) of Table 2, the values are higher in column B than in column A. Referring to column (I) of Table 2, a comparison between the values: "Content of Dead Cells in Total Nucleated Cells" and "Content of Dead Mononuclear Cells in Total Nucleated Cells" in column B indicates that the content of the dead mononuclear cells is higher than that of the dead granulocytes. Referring to column (II), a comparison between the values: "Content of Dead Cells in Total Nucleated Cells" and "Content of Dead Mononuclear Cells in Total Nucleated Cells" in column B indicates that the content of the dead granulocytes is higher than that of the dead mononuclear cells.

From the results shown in FIGS. 9A, 9B, 10A, and 10B, and Tables 1 and 2, it has been shown that the longer the time for which peripheral blood is allowed to stand, the lower the viability of the cells contained in the peripheral blood. It has also been shown that concerning peripheral blood (I) with a very high lymphocyte content, dead mononuclear cells are predominantly contained in the peripheral blood allowed to stand for a long time. It has also been shown that concerning peripheral blood (II) with a very high granulocyte content, dead granulocytes are predominantly contained in the peripheral blood allowed to stand for a long time.

MEASUREMENT EXAMPLE 2

In this measurement example, peripheral blood was collected from a healthy subject and allowed to stand at room temperature for 2 or 32 hours before used as an analyte.

Figure 11:
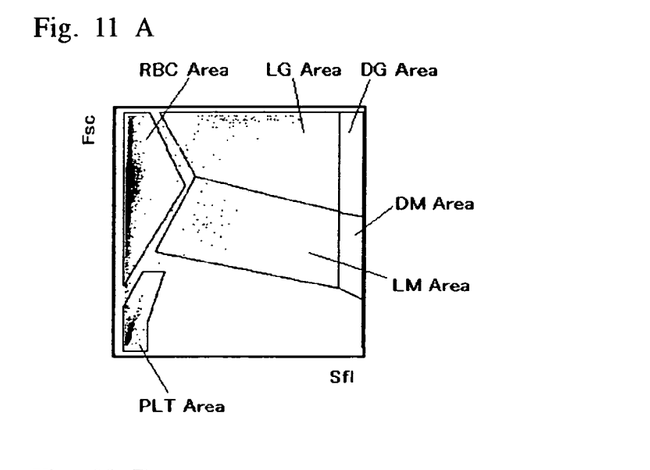

The scattergrams as shown in FIGS. 11A and 11B were obtained using the cell analysis apparatus 1 as described above. FIG. 11A shows the result of the measurement in which the peripheral blood was allowed to stand at room temperature for 2 hours after the collection, and FIG. 11B shows the result of the measurement in which the peripheral blood was allowed to stand at room temperature for 32 hours after the collection.

Table 3 shows the count values obtained in step S10 of the analysis process using the cell analysis apparatus 1 as described above, which include "the number of living mononuclear cells," "the number of dead mononuclear cells," "the number of living granulocytes," and "the number of dead granulocytes." Each value with respect to each item in Table 3 is based on the count of dots found in LM, DM, LG, or DG area on each of the scattergrams of FIGS. 11A and 11B. In Table 3, "the number of living mononuclear cells" is represented by LM, "the number of dead mononuclear cells" by DM, "the number of living granulocytes" by LG, and "the number of dead granulocytes" by DG. In Table 3, column A shows the results of measurement of the peripheral blood that was allowed to stand at room temperature for 2 hours after the collection, and column B shows the results of measurement of the peripheral blood that was allowed to stand at room temperature for 32 hours after the collection.

TABLE 3

|  | Number of Cells Contained Per 1 μL of Analyte | |
| --- | --- | --- |
|  | A | B |
| LM | 2171 | 1982 |
| DM | 0 | 189 |
| LG | 5609 | 5092 |
| DG | 0 | 517 |

Referring to FIGS. 11A and 11B and Table 3, a comparison between columns A and B indicates that the number of dead cells (dead mononuclear cells and dead granulocytes) is greater in column B than in column A.

Table 4 shows the values calculated in step S10 of the analysis process using the cell analysis apparatus 1 as described above, which include "the content of dead cells in the total nucleated cells," "the content of dead mononuclear cells in the total nucleated cells" and "the content of dead mononuclear cells in the total mononuclear cells." Each value with respect to each item in Table 4 is calculated according to the formulae as used in Measurement Example 1 from "the number of living mononuclear cells," "the number of dead mononuclear cells," "the number of living granulocytes," and "the number of dead granulocytes" in Table 3. In Table 4, column A shows the results of measurement of the peripheral blood that was allowed to stand at room temperature for 2 hours after the collection, and column B shows the results of measurement of the peripheral blood that was allowed to stand at room temperature for 32 hours after the collection.

TABLE 4

|  | A | B |
| --- | --- | --- |
| Content of Dead Cells in Total Nucleated Cells (%) | 0.0 | 9.1 |
| Content of Dead Mononuclear Cells in Total Nucleated Cells (%) | 0.0 | 2.4 |
| Content of Dead Mononuclear Cells in Total Mononuclear Cells (%) | 0.0 | 8.7 |

In Table 4, the value is higher in column B than in column A with respect to every item. A comparison between the values: "Content of Dead Cells in Total Nucleated Cells" and "Content of Dead Mononuclear Cells in Total Nucleated Cells" in column B indicates that the content of the dead granulocytes is higher than that of the dead mononuclear cells.

MEASUREMENT EXAMPLE 3

Like bone marrow, cord blood is known to be rich in hematopoietic stem cells. In this measurement example, therefore, cord blood was used which was collected from the umbilical cord of a healthy subject at the time of delivery. After the collection, red blood cells were removed from the cord blood by centrifugation (at a rotation speed of about 3000 rpm for 20 minutes at a temperature of 10° C.), and the resulting residue was used as an analyte in the measurement.

Figure 12:
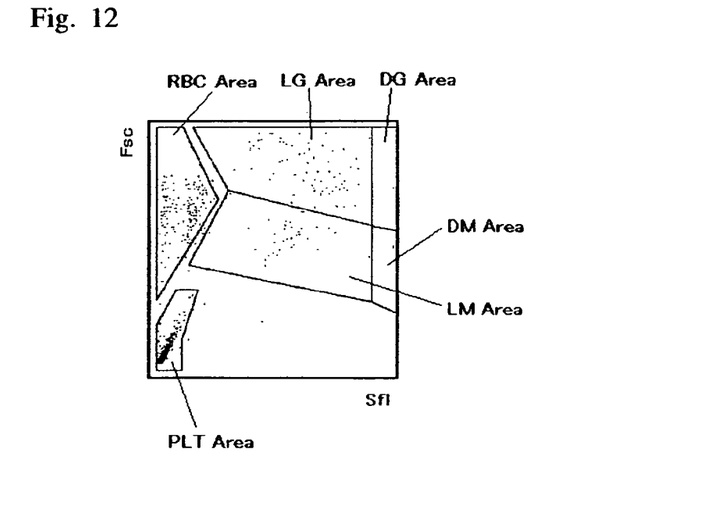

The scattergram as shown in FIG. 12 was obtained using the cell analysis apparatus 1 as described above.

Table 5 shows the count values obtained in step S10 of the analysis process using the cell analysis apparatus 1 as described above, which include "the number of living mononuclear cells," "the number of dead mononuclear cells," "the number of living granulocytes," and "the number of dead granulocytes." Each value with respect to each item in Table 5 is based on the count of dots found in LM, DM, LG, or DG area on the scattergram of FIG. 12. In Table 5, "the number of living mononuclear cells" is represented by LM, "the number of dead mononuclear cells" by DM, "the number of living granulocytes" by LG, and "the number of dead granulocytes" by DG.

TABLE 5

|  | Number of Cells Contained Per 1 µL of Analyte |
| --- | --- |
| LM | 2321 |
| DM | 61 |
| LG | 4565 |

Table 6 shows the values calculated in step S10 of the analysis process using the cell analysis apparatus 1 as described above, which include "the content of dead cells in the total nucleated cells," "the content of dead mononuclear cells in the total nucleated cells" and "the content of dead mononuclear cells in the total mononuclear cells." These values are calculated according to the formulae as used in Measurement Example 1 from "the number of living mononuclear cells," "the number of dead mononuclear cells," "the number of living granulocytes," and "the number of dead granulocytes" in Table 5.

TABLE 6

| Content of Dead Cells in Total Nucleated Cells (%) | 1.8 |
| --- | --- |
| Content of Dead Mononuclear Cells in Total Nucleated Cells (%) | 0.9 |
| Content of Dead Mononuclear Cells in Total Mononuclear Cells (%) | 2.6 |

The number of the dots found in DM area (the dead mononuclear cell-representing area) on the scattergram of FIG. 12, the value with respect to DM (the number of the dead mononuclear cells) in Table 5, and the value of "Content of Dead Mononuclear Cells in Total Nucleated Cells" in Table 6 indicate that the content of the dead mononuclear cells is very low in the analyte used in this measurement example. In addition, the value of "Content of Dead Mononuclear Cells in Total Mononuclear Cells" in Table 6 indicates that the content of the dead mononuclear cells in the total mononuclear cells is relatively low in the analyte and thus that the viability of the mononuclear cells is relatively high.

The number of dots in the red blood cell-representing area (RBC area) on the scattergram of FIG. 12 indicates that some red blood cells remain in the analyte even after the centrifugation, which has been performed after the collection. The numbers of the dots in the blood platelet-representing area (PLT area) and the granulocyte-representing areas (LG and DG areas) on the scattergram of FIG. 12 indicate that the analyte also contains blood platelets and granulocytes. According to this embodiment, therefore, not only mononuclear cells but also blood cell components such as red blood cells, blood platelets and granulocytes can be identified at the same time. Thus, it can be determined not only how much mononuclear cells necessary for therapy are contained in the analyte but also how much cells unnecessary for cell therapy are contained in the analyte. Cell materials such as blood contain not only mononuclear cells necessary for cell therapy but also other cells unnecessary for cell therapy (e.g. blood cell components such as red blood cells, granulocytes and platelets). Such cells unnecessary for therapy in cell materials can cause a side effect during transplantation, and thus it has been desired to remove such unnecessary cells from the cell materials as much as possible. For safe practice of cell therapy, it should be important to check each cell unnecessary for cell therapy in the analyte.

Peripheral blood or cord blood is used as an analyte in above each measurement example, while any other material may also be used as an analyte in the invention. Any fluid potentially containing mononuclear cells may be used in the invention. Examples of such a fluid include bone marrow and a liquid culture obtained by stem cell culture.

RET-SEARCH(II)DYE manufactured by Sysmex Corporation is used as a dyeing solution in above each measurement example, while any other staining material may also be used in the invention. Any dyeing solution containing any nucleic acid-staining dye with membrane permeability may be used in the invention. Examples of the nucleic acid-staining dye with membrane permeability include Auramine O and Oxazine 720.

The process of identifying various types of cells in the cell analysis apparatus 1 according to the embodiment includes the steps of preparing a scattergram for analysis and defining, on the prepared scattergram, a specific area that represents each type of cells, while the process may include any other steps according to the invention. For example, the process may include the steps of previously setting specific values of forward scattered light intensity and fluorescence intensity with respect to each type of cells and comparing measurements of forward scattered light intensity and fluorescence intensity with the specific values so that each type of cells can be identified.

The calculations obtained in the analysis step using the cell analysis apparatus 1 according to the embodiment include "the content of dead cells in the total nucleated cells," "the content of dead mononuclear cells in the total nucleated cells" and "the content of dead mononuclear cells in the total mononuclear cells," while any other calculation may be obtained according to the invention. For example, "the content of dead cells in the total cells" may be calculated.

For example, Formula 4 is for the calculation of "the content of dead cells in the total cells." The count of the total dots found in a scattergram may be used as the total number of the cells. Alternatively, the sum of the counts of the dots found in LM, DM, LG, DG, RBC, and PLT areas, respectively, on the scattergram may be used as the total number of the cells.

(DM+DG)/(Total Number of Cells)×100(%)  Formula 4:

In the invention, "the viability of mononuclear cells" may also be calculated.

For example, "the viability of mononuclear cells" may be calculated according to Formula 5, which produces the rate of living mononuclear cells in the total mononuclear cells (the content of living cells in the total mononuclear cells).

LM/(LM+DM)×100(%)  Formula 5:

In the invention, "the content of each type of cells (living mononuclear cells, dead mononuclear cells, living granulocytes, dead granulocytes, red blood cells, or blood platelets) in the total cells" may also be calculated.

For example, "the content of living mononuclear cells in the total cells" may be calculated according to Formula 6.

LM/(Total Number of Cells)×100(%)  Formula 6:

For example, "the content of dead mononuclear cells in the total cells" may be calculated according to Formula 7.

DM/(Total Number of Cells)×100(%)  Formula 7:

For example, "the content of living granulocytes in the total cells" may be calculated according to Formula 8.

LG/(Total Number of Cells)×100(%)  Formula 8:

For example, "the content of dead granulocytes in the total cells" may be calculated according to Formula 9.

DG/(Total Number of Cells)×100(%)  Formula 9:

For example, "the content of red blood cells in the total cells" may be calculated according to Formula 10.

RBC/(Total Number of Cells)×100(%)  Formula 10:

For example, "the content of blood platelets in the total cells" may be calculated according to Formula 11.

PLT/(Total Number of Cells)×100(%)  Formula 11:

The "content of living granulocytes in the total cells," "the content of dead granulocytes in the total cells," "the content of red blood cells-in the total cells," and "the content of blood platelets in the total cells" indicate the content of cells unnecessary for therapy in the analyte. Cells unnecessary for therapy and present as contaminants in cell materials can cause side effects or rejection. For safe practice of cell therapy, therefore, it should be important to check the values: "the content of living granulocytes in the total cells," "the content of dead granulocytes in the total cells," "the content of red blood cells in the total cells," and "the content of blood platelets in the total cells."

In the invention, a hematocrit value may also be calculated. The hematocrit value represents the ratio of red blood cell volume in blood. Like "the content of red blood cells in the total cells," the hematocrit value indicates the content of red blood cells in the analyte. For safe practice of cell therapy, it should be important to check this value. For example, hematocrit may be calculated by the following method. First, the volume of each cell classified and counted as red blood cell is calculated based on forward scattering intensity. The calculated volumes of the respective red blood cells are totaled to give the volume (RV) of the red blood cells in the analyte. A hematocrit value (%) can be calculated from RV and the volume (V) of the analyte according to such a calculation formula as Formula 12.

RV/V×100(%)  Formula 12:

The analysis step in the cell analysis apparatus 1 according to the embodiment includes setting LM, DM, LG, DG, RBC, and PLT areas in the scattergram and counting the cells in each area, while any other analysis step may be used in the invention. For example, the operator may choose and decide whether or not to count cells with respect to each type of cells. For example, this method may include the steps of: storing, into the memory part 33 as shown in FIG. 5, analysis programs that allow the operator to choose and decide whether or not setting should be made on the scattergram with respect to each of LM, DM, LG, DG, RBC, and PLT areas; allowing the analysis part 34 to perform an analysis process based on the analysis programs; and counting the cells in the chosen area.

The analysis step in the cell analysis apparatus 1 according to the embodiment includes counting the cells found in the scattergram and calculating "the content of dead cells in the total nucleated cells," "the content of dead mononuclear cells in the total nucleated cells" and "the content of dead mononuclear cells in the total mononuclear cells," while any other analysis step may be used in the invention. In addition, it may be determined whether or not the analyte is effective for cell therapy, based on the results of the count and calculation as described above.

Figure 13:
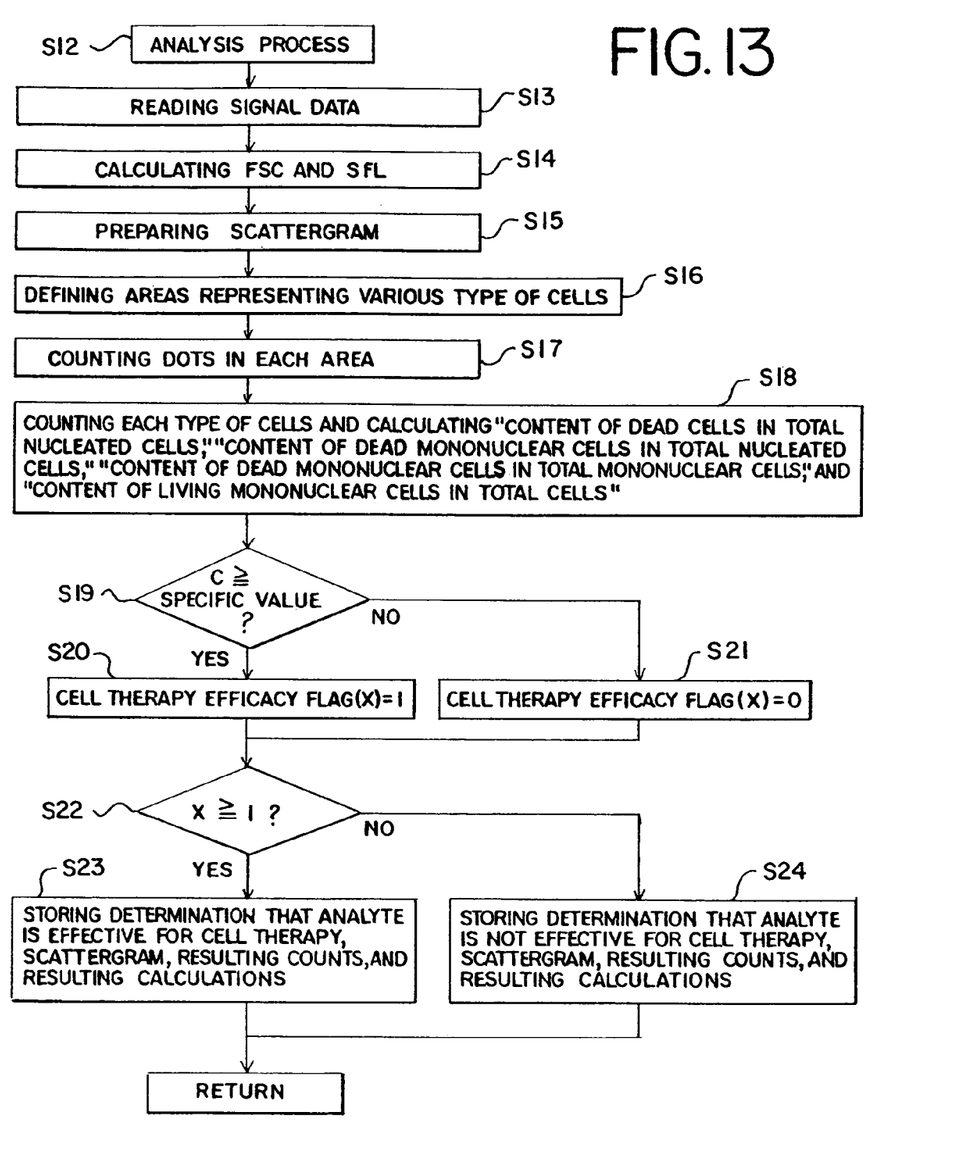
FIG. 13 is a diagram illustrating a flow of an analysis process in a cell analysis apparatus according to another embodiment of the invention.

For example, a method of determining whether or not the analyte is effective for cell therapy includes the step of determining whether or not the analyte is effective for cell therapy based on the value of "the content of living mononuclear cells in the total cells." In this method, a predetermined specific value is provided with respect to "the content of living mononuclear cells in the total cells," which is calculated according to Formula 6 as shown above. If the calculated value of "the content of living mononuclear cells in the total cells" is less than the specific value, it is determined that the analyte is not effective for cell therapy. If not less than the specific value, it is determined that the analyte is effective for cell therapy. A flow chart for the analysis process according to this method is shown in FIG. 13. Each step in the flow chart is described below, though a description of steps S13 to S17 is omitted because they are the same as steps S5 to S9 in FIG. 7 as described above.

S18: The number of each type of cells is determined based on the count of the dots in each area as given in S17. The counts of the cells are also used for the calculation of "the content of dead cells in the total nucleated cells," "the content of dead mononuclear cells in the total nucleated cells," "the content of dead mononuclear cells in the total mononuclear cells," and "the content of living mononuclear cells in the total cells." The process then proceeds to S19.

S19: A comparison is made between a predetermined specific value and the value C of "the content of living mononuclear cells in the total cells" calculated in S18. If the calculated value C is not less than the specific value, the process then proceeds to S20. If the value C is less than the specific value, the process then proceeds to S21.

S20: The cell therapy efficacy flag X is set at "1." The process then proceeds to S22.

S21: The cell therapy efficacy flag X is set at "0." The process then proceeds to S22.

S22: In S22, it is determined whether or not the cell therapy efficacy flag X is "1." If the cell therapy efficacy flag X is "1," the process proceeds to S23. If the cell therapy efficacy flag X is "0," the process proceeds to S24.

S23: Stored are the determination that the analyte is effective for cell therapy, the data of the scattergram prepared in S15 and S16, and the data of the counts and the calculations obtained in S18.

S24: Stored are the determination that the analyte is not effective for cell therapy, the data of the scattergram prepared in S15 and S16, and the data of the counts and the calculations obtained in S18.

Figure 14:
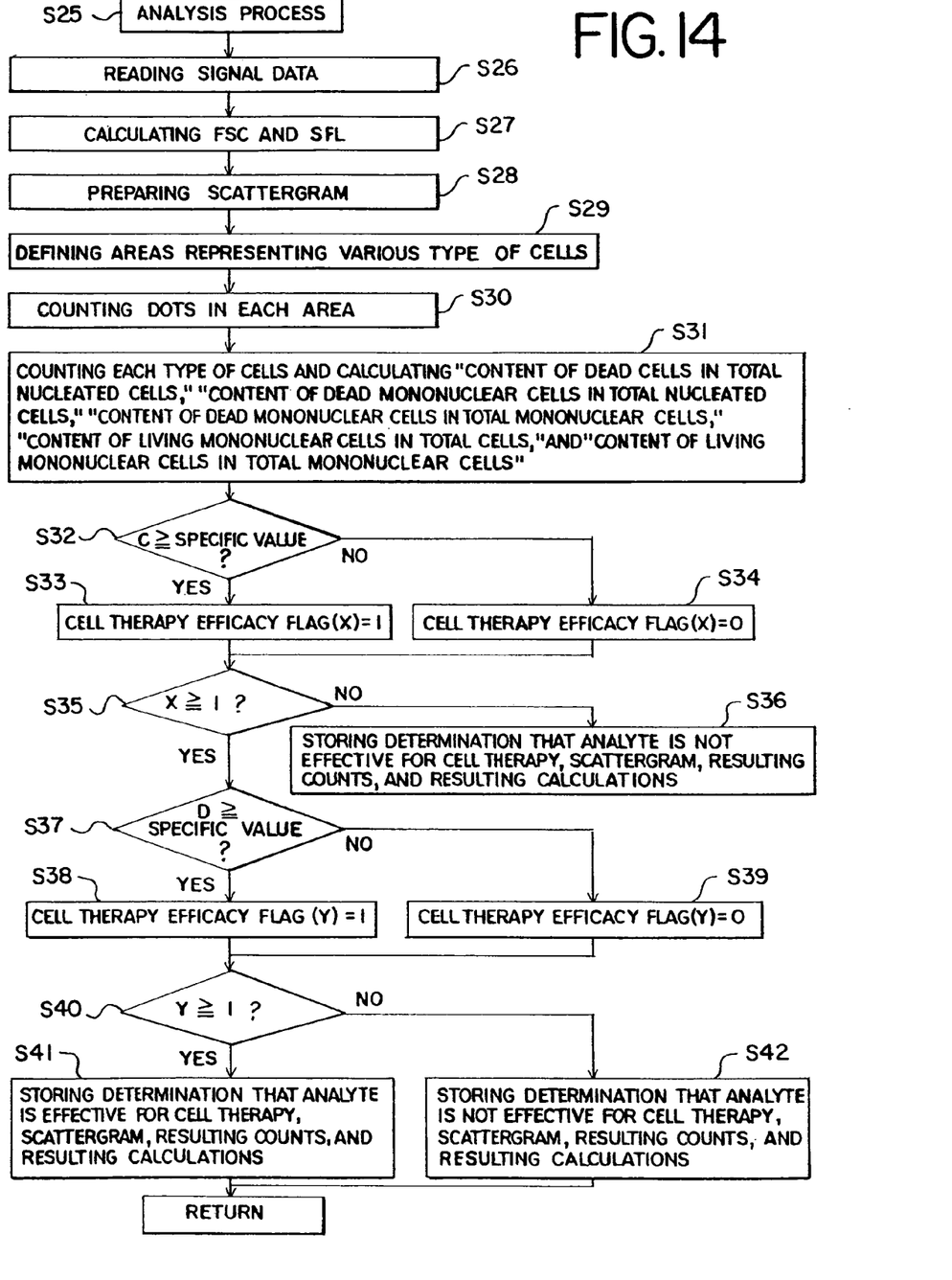
FIG. 14 is a diagram illustrating a flow of an analysis process in a cell analysis apparatus according to yet another embodiment of the invention.

Another method of determining whether or not the analyte is effective for cell therapy includes the step of determining whether or not the analyte is effective for cell therapy based on the values of "the content of living mononuclear cells in the total cells" and "the content of living mononuclear cells in the total mononuclear cells." In this method, predetermined specific values are provided with respect to "the content of living mononuclear cells in the total cells" which is calculated according to Formula 6 as described above and with respect to "the content of living mononuclear cells in the total mononuclear cells" which is calculated according to Formula 5 as described above, respectively. First, if the calculated value of "the content of living mononuclear cells in the total cells" is less than the specific value with respect to "the content of living mononuclear cells in the total cells," it is determined that the analyte is not effective for cell therapy. If the calculated value of "the content of living mononuclear cells in the total cells" is not less than the specific value, the calculated value of "the content of living mononuclear cells in the total mononuclear cells" is then compared with the specific value with respect to "the content of living mononuclear cells in the total mononuclear cells." If the calculated value is less than the specific value with respect to "the content of living mononuclear cells in the total mononuclear cells," it is determined that the analyte is not effective for cell therapy. If not less than the specific value, it is determined that the analyte is effective for cell therapy. A flow chart for the analysis process according to this method is shown in FIG. 14. Each step in the flow chart is described below, though a description of steps S26 to S30 is omitted because they are the same as steps S5 to S9 in FIG. 7 as described above.

S31: The number of each type of cells is determined based on the count of the dots in each area as given in S30. The counts of the cells are also used for the calculation of "the content of dead cells in the total nucleated cells," "the content of dead mononuclear cells in the total nucleated cells," "the content of dead mononuclear cells in the total mononuclear cells," "the content of living mononuclear cells in the total cells," and "the content of living mononuclear cells in the total mononuclear cells." The process then proceeds to S32.

S32: A comparison is made between a predetermined specific value and the value C of "the content of living mononuclear cells in the total cells" calculated in S31. If the calculated value C is not less than the specific value, the process then proceeds to S33. If the value C is less than the specific value, the process then proceeds to S34.

S33: The cell therapy efficacy flag X is set at "1." The process then proceeds to S35.

S34: The cell therapy efficacy flag X is set at "0." The process then proceeds to S35.

S35: In S35, it is determined whether or not the cell therapy efficacy flag X is "1." If the cell therapy efficacy flag X is "1," the process proceeds to S37. If the cell therapy efficacy flag X is "0," the process proceeds to S36.

S36: Stored are the determination that the analyte is not effective for cell therapy, the data of the scattergram prepared in S28 and S29, and the data of the counts and the calculations obtained in S31.

S37: A comparison is made between a predetermined specific value and the value D of "the content of living mononuclear cells in the total mononuclear cells" calculated in S31. If the calculated value D is not less than the specific value, the process then proceeds to S38. If the value D is less than the specific value, the process then proceeds to S39.

S38: The cell therapy efficacy flag Y is set at "1." The process then proceeds to S40.

S39: The cell therapy efficacy flag Y is set at "0." The process then proceeds to S40.

S40: In S40, it is determined whether or not the cell therapy efficacy flag Y is "1." If the cell therapy efficacy flag Y is "1," the process proceeds to S41. If the cell therapy efficacy flag Y is "0," the process proceeds to S42.

S41: Stored are the determination that the analyte is effective for cell therapy, the data of the scattergram prepared in S28 and S29, and the data of the counts and the calculations obtained in S31.

S42: Stored are the determination that the analyte is not effective for cell therapy, the data of the scattergram prepared in S28 and S29, and the data of the counts and the calculations obtained in S31.

Analysis programs for performing the above determination process are stored in the memory part 33, and based on the analysis programs, the analysis process is performed in the analysis part 34 so that it can automatically be determined whether or not the analyte is effective for cell therapy. The resulting determination may be output and displayed on the liquid-crystal touch panel 2 together with the scattergram, the count of each type of cells, and the calculations of "the content of dead cells in the total nucleated cells," "the content of dead mononuclear cells in the total nucleated cells" and "the content of dead mononuclear cells in the total mononuclear cells."

What is claimed is:

1. A cell analysis apparatus for analyzing cells contained in an analyte, comprising:
    a test sample preparation unit for preparing a test sample comprising the analyte treated with at least a nucleic acid-staining dye for staining an intracellular substance of the cells in the analyte;
    a detection unit for detecting scattered light and fluorescence from each cell in the test sample; and
    a controller configured for performing operations comprising:
        classifying the cells into a plurality of cell groups based on the scattered light and the fluorescence detected by the detection unit, wherein the plurality of cell groups comprises a living mononuclear cell group and a dead mononuclear cell group; and
        counting the classified cells in the living mononuclear cell group as living mononuclear cells, wherein the living mononuclear cells comprise living stem cells and living lymphocytes.

2. The cell analysis apparatus of claim 1, wherein the operations further comprise preparing a two-dimensional distribution chart based on intensity of the scattered light and intensity of the fluorescence, and displaying an area of the living mononuclear cell group and an area of the dead mononuclear cell group on the two-dimensional distribution chart.

3. The cell analysis apparatus of claim 1, wherein the operations further comprise counting the classified cells in the dead mononuclear cell group as dead mononuclear cells.

4. The cell analysis apparatus of claim 3, wherein the operations further comprise calculating viability of the mononuclear cells based on resultant counts of the living mononuclear cells and the dead mononuclear cells.

5. The cell analysis apparatus of claim 1, wherein the plurality of cell groups further comprises a living granulocyte group, a dead granulocyte group, a red blood cell group, and a blood platelet group.

6. The cell analysis apparatus of claim 5, wherein the operations further comprise:

counting the classified cells in the living granulocyte group as living granulocytes and the classified cells in the dead granulocyte group as dead granulocytes; and calculating viability of the granulocytes based on resultant counts of the living granulocytes and the dead granulocytes.

7. The cell analysis apparatus of claim 5, wherein the operations further comprise:

counting the classified cells in the dead mononuclear cell group as dead mononuclear cells, the classified cells in the living granulocyte group as living granulocytes, and the classified cells in the dead granulocyte group as dead granulocyte; and calculating a ratio of a total number of the dead mononuclear cells and the dead granulocytes to a total number of the living mononuclear cells, the dead mononuclear cells, the living granulocytes, and the dead granulocytes based on resultant counts of the living mononuclear cells, the dead mononuclear cells, the living granulocytes, and the dead granulocytes.

8. The cell analysis apparatus of claim 5, wherein the operations further comprise:

counting the classified cells in the red blood cell group as red blood cells; and calculating a hematocrit based on a resulting count of the red blood cells.

9. The cell analysis apparatus of claim 5, wherein the operations further comprise counting the classified cells in the dead mononuclear cell group as dead mononuclear cells, the classified cells in the living granulocyte group as living granulocytes, the classified cells in the dead granulocyte group as dead granulocytes, the classified cells in the red blood cell group as red blood cells, and the classified cells in the blood platelet group as blood platelets.

10. The cell analysis apparatus of claim 9, wherein the operations further comprise calculating a ratio of a number of the living mononuclear cells, the dead mononuclear cells, the living granulocytes, the dead granulocytes, the red blood cells or the blood platelets to a total number of the living mononuclear cells, the dead mononuclear cells, the living granulocytes, the dead granulocytes, the red blood cells, and the blood platelets.

11. The cell analysis apparatus of claim 10, wherein the operations further comprise determining whether or not the analyte is effective for cell therapy based on a calculated result.

* * * * *